(12) United States Patent
Maitland et al.

(10) Patent No.: US 11,020,507 B2
(45) Date of Patent: *Jun. 1, 2021

(54) HEMORRHAGE MANAGEMENT SYSTEM

(71) Applicants: LAWRENCE LIVERMORE NATIONAL SECURITY, LLC, Livermore, CA (US); THE TEXAS A&M UNIVERSITY SYSTEM, College Station, TX (US)

(72) Inventors: Duncan J. Maitland, College Station, TX (US); Todd Lawrence Landsman, College Station, TX (US); Tyler Joseph Touchet, Cypress, TX (US); Elizabeth L. Cosgriff-Hernandez, College Station, TX (US); Thomas S. Wilson, San Leandro, CA (US)

(73) Assignees: LAWRENCE LIVERMORE NATIONAL SECURITY, LLC, Livermore, CA (US); THE TEXAS A&M UNIVERSITY SYSTEM, College Station, TX (US)

( * ) Notice: Subject to any disclaimer, the term of this patent is extended or adjusted under 35 U.S.C. 154(b) by 130 days.

This patent is subject to a terminal disclaimer.

(21) Appl. No.: 16/353,793

(22) Filed: Mar. 14, 2019

(65) Prior Publication Data
US 2019/0209730 A1    Jul. 11, 2019

Related U.S. Application Data

(63) Continuation of application No. 14/661,215, filed on Mar. 18, 2015, now Pat. No. 10,265,433.

(51) Int. Cl.
*A61L 15/42* (2006.01)
*A61F 13/00* (2006.01)
(Continued)

(52) U.S. Cl.
CPC ............... *A61L 15/18* (2013.01); *A61L 15/26* (2013.01); *A61L 15/425* (2013.01); *A61L 15/46* (2013.01);
(Continued)

(58) Field of Classification Search
CPC ................................. A61L 15/18; A61L 15/26
See application file for complete search history.

(56) References Cited

U.S. PATENT DOCUMENTS

| 6,034,149 A | * | 3/2000 | Bleys ..................... C08J 9/0061 |
| | | | 521/155 |
| 6,583,194 B2 | * | 6/2003 | Sendijarevic ...... C08G 18/4211 |
| | | | 521/170 |

(Continued)

OTHER PUBLICATIONS

Gurevitch, et al. "Shape memory polymer foams from emulsion templating", Soft Matter, 2012, pp. 10378-10387, vol. 8, the Royal Society of Chemistry.
(Continued)

*Primary Examiner* — Tatyana Zalukaeva
*Assistant Examiner* — Jessica R Arble
(74) *Attorney, Agent, or Firm* — Trop, Pruner & Hu, P.C.

(57) ABSTRACT

An embodiment includes a wound dressing comprising: a shape memory polymer (SMP) foam, including open cells, having first and second states; and a hydrogel (HG) included within the cells; wherein (a) in a first position a composite, including the SMP foam and the HG, is configured to be located proximate a hemorrhagic tissue with the SMP foam in the first state; (b) in a second position the composite is configured to be expanded to the second state against the hemorrhagic tissue when the SMP foam is plasticized at 37° C. depressing a glass transition temperature ($T_g$) of the SMP foam to below 25° C. Other embodiments are described herein.

20 Claims, 7 Drawing Sheets

(51) Int. Cl.
*A61L 15/18* (2006.01)
*A61L 15/26* (2006.01)
*A61L 15/46* (2006.01)
*A61L 24/00* (2006.01)

(52) U.S. Cl.
CPC ....... *A61L 24/0015* (2013.01); *A61L 24/0036* (2013.01); *A61L 24/0094* (2013.01); *A61F 13/00017* (2013.01); *A61L 2300/106* (2013.01); *A61L 2300/404* (2013.01); *A61L 2400/16* (2013.01)

(56) References Cited

U.S. PATENT DOCUMENTS

| | | | |
|---|---|---|---|
| 8,269,058 | B2 | 9/2012 | McCarthy |
| 8,450,554 | B2 | 5/2013 | Robinson et al. |
| 8,741,335 | B2 | 6/2014 | McCarthy |
| 8,921,435 | B2 * | 12/2014 | Silverstein ............... C08J 9/283 521/99 |
| 10,265,433 | B2 * | 4/2019 | Maitland ............. A61L 24/0094 |
| 2003/0040699 | A1 | 2/2003 | Talling et al. |
| 2006/0036045 | A1 | 2/2006 | Wilson et al. |
| 2006/0154195 | A1 | 7/2006 | Mather et al. |
| 2006/0292244 | A1 | 12/2006 | Reimer et al. |
| 2008/0033334 | A1 | 2/2008 | Gurtner et al. |
| 2010/0042144 | A1 * | 2/2010 | Bennett .............. A61B 17/0401 606/213 |
| 2010/0057009 | A1 | 3/2010 | McQueen et al. |
| 2011/0039967 | A1 | 2/2011 | Wilson |
| 2013/0253634 | A1 | 9/2013 | Wilson |
| 2014/0121295 | A1 | 5/2014 | Gall |
| 2014/0142523 | A1 | 5/2014 | Steinbaugh |

OTHER PUBLICATIONS

Michael S. Silverstein, "PolyHIPEs: Recent advances in emulsion-templated porous polymers", Progress in Polymer Science, 2013, pp. 199-234, vol. 39, El Sevier, Ltd.

International Search Report and Written Opinion for PCT/US16/21938, corresponding to U.S. Appl. No. 14/661,215, 16 pages.

Xiao, et al. "Novel multifunctional NaYF4:Er3+,Yb3+/PEGDA hybrid microspheres: NIR-light-activated photopolymerization and drug delivery", Feb. 21, 2013, pp. 1527-1529, vol. 49, Issue 15, Chemical Communications.

Wedmore, Ian, et al., "A Special Report on the Chitosan-based Hemostatic Dressing: Experience in Current Combat Operations," The Journal of Trauma, vol. 60, No. 3, Mar. 2006, 5 Pages.

Kheirabadi, Bijan, "Evaluation of Topical Hemostatic Agents for Combat Wound Treatment," The Army Medical Department Journal, http://www.cs.amedd.army.mil/dasqaDocuments.aspx?type=1, Apr.-Jun. 2011, 14 Pages.

Revmedx, Inc., "De Novo Classification Request for XSTAT," Jan. 2013, Washington, D.C., 16 Pages.

* cited by examiner

| Sample | Tm of Hydrogel | Tm of Composite |
|---|---|---|
| PEG6k 5wt% | 48.97°C | 42.03°C |
| PEG6k 10wt% | 51.66°C | 47.39°C |
| PEG10k 5wt% | 57.13°C | 49.99°C |
| PEG10k 10wt% | 53.53°C | 51.88°C |

Figure 2(b)

| Sample | Pre Crimp Dia (mm) | Crimped Dia (mm) | Dia. After 15 min | % Shape Recovery | % Strain Recovery |
|---|---|---|---|---|---|
| Control | 5.57 | 0.74 | 6.00 | 107.75 | 716.59 |
| PEG6k 5wt% | 5.89 | 1.33 | 6.98 | 118.57 | 424.66 |
| PEG6k 10wt% | 6.09 | 1.85 | 7.42 | 121.87 | 301.03 |

HEMORRHAGE MANAGEMENT SYSTEM

This application is a continuation of U.S. patent application Ser. No. 14/661,215, filed Mar. 18, 2015, and entitled "Hemorrhage Management System". The content of the above application is hereby incorporated by reference.

STATEMENT AS TO RIGHTS TO APPLICATIONS MADE UNDER FEDERALLY SPONSORED RESEARCH AND DEVELOPMENT

The United States Government has rights in this application pursuant to Contract No. DE-AC52-07NA27344 between the United States Department of Energy and Lawrence Livermore National Security, LLC for the operation of Lawrence Livermore National Laboratory.

BACKGROUND

Field of Endeavor

The present application relates to hemorrhages and more particularly to a hemorrhage management system.

State of Technology

This section provides background information related to the present disclosure which is not necessarily prior art.

Approximately 50% of combat and 80% of civilian trauma fatalities are due to uncontrolled hemorrhage. Exsanguination is a leading cause of pre-hospital death. An estimated 80% of trauma wounds are not amenable to compression or tourniquets. To treat such hemorrhage conditions, there are at least three conventional hemorrhage control systems: compression (applying pressure directly to a wound), hemostatic gauze (incorporating procoagulants to minimize time to hemostasis), and expandable foams (used to expand within a wound and direct pressure on the wound).

SUMMARY

Features and advantages of the disclosed apparatus, systems, and methods will become apparent from the following description. Applicant is providing this description, which includes drawings and examples of specific embodiments, to give a broad representation of the apparatus, systems, and methods. Various changes and modifications within the spirit and scope of the application will become apparent to those skilled in the art from this description and by practice of the apparatus, systems, and methods. The scope of the apparatus, systems, and methods is not intended to be limited to the particular forms disclosed and the application covers all modifications, equivalents, and alternatives falling within the spirit and scope of the apparatus, systems, and methods as defined by the claims.

The scope of the disclosed apparatus, systems, and methods comprises all of the features of novelty of the hemorrhage management system as shown and described.

The apparatus, systems, and methods are susceptible to modifications and alternative forms. Specific embodiments are shown by way of example. It is to be understood that the apparatus, systems, and methods are not limited to the particular forms disclosed. The apparatus, systems, and methods cover all modifications, equivalents, and alternatives falling within the spirit and scope of the application as defined by the claims.

BRIEF DESCRIPTION OF THE DRAWINGS

The accompanying drawings, which are incorporated into and constitute a part of the specification, illustrate specific embodiments of the apparatus, systems, and methods and, together with the general description given above, and the detailed description of the specific embodiments, serve to explain the principles of the apparatus, systems, and methods. Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

FIGS. 2(a) and 2(b) depict tunability of embodiments of the invention based on hydrogel composition.

DETAILED DESCRIPTION OF SPECIFIC EMBODIMENTS

Figure 1:
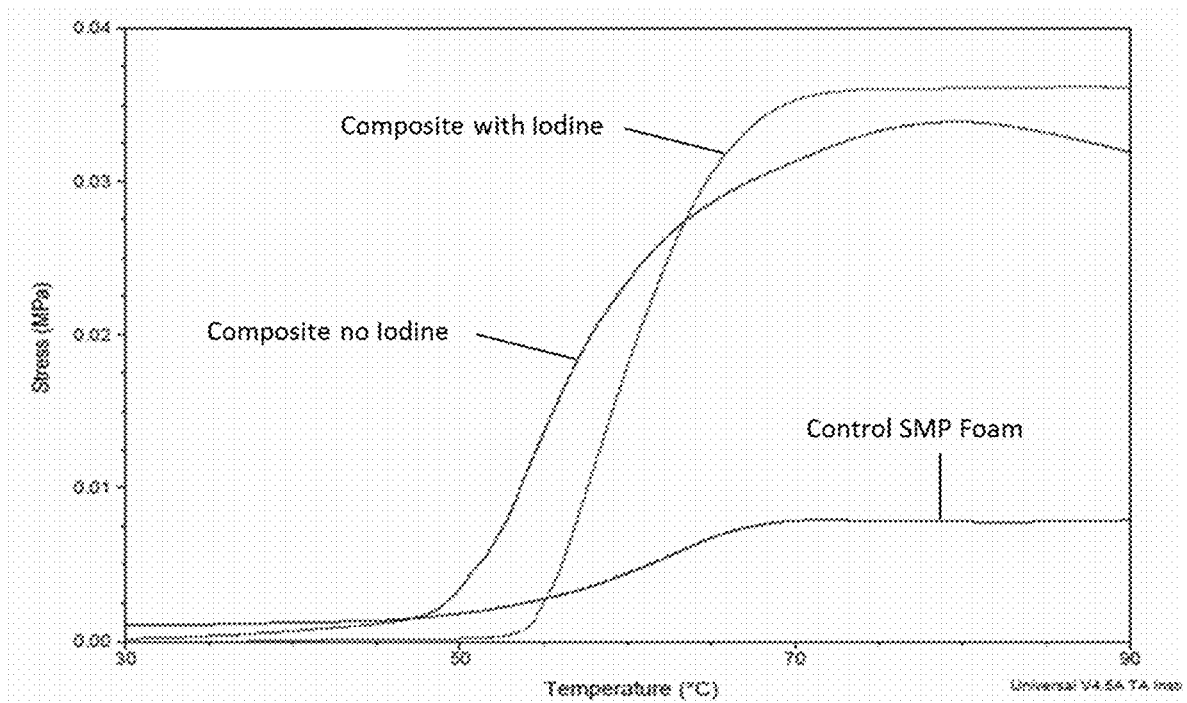
FIG. 1 depicts expansion force vs. temperature for various embodiments of the invention.

Referring to the drawings, to the following detailed description, and to incorporated materials, detailed information about the apparatus, systems, and methods is provided including the description of specific embodiments. The detailed description serves to explain the principles of the apparatus, systems, and methods. The apparatus, systems, and methods are susceptible to modifications and alternative forms. The application is not limited to the particular forms disclosed. The application covers all modifications, equivalents, and alternatives falling within the spirit and scope of the apparatus, systems, and methods as defined by the claims.

Reference will now be made to the drawings wherein like structures may be provided with like suffix reference designations. In order to show the structures of various embodiments more clearly, the drawings included herein are diagrammatic representations of structures. Thus, the actual appearance of the structures, for example in an image, may appear different while still incorporating the claimed structures of the illustrated embodiments. Moreover, the drawings may only show the structures useful to understand the illustrated embodiments. Additional structures known in the art may not have been included to maintain the clarity of the drawings. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical or electrical contact with each other and "coupled" may indicate elements co-operate or interact with each other, but they may or may not be in direct physical or electrical contact.

Compression is lacking in that it does not reduce risk of infection, is only applicable to specific wounds, and has an extended time to clot formation. Hemostatic gauze is not ideal because it can cause thermal tissue damage, does not reduce the risk of infection, is vulnerable to high rebleed rates, and has the potential to cause systemic exposure of the procoagulant. Conventional expandable foams are problematic because they are difficult to remove from the wound, do not reduce the risk of infection, and have limited efficacy data.

In contrast, an embodiment satisfies various characteristics for superior hemorrhage management system such as: (1) stops severe arterial/venous bleeding in less than 2 minutes, (2) swells to absorb wound exudate, (3) is flexible enough to conform to complex wound geometries, and (4) protects against bacterial infection. One such embodiment includes a composite comprising a shape memory polymer (SMP) foam and a Poly(ethylene gylcol) Diacrylate (PEG-DA) N-vinylpyrrolidone (NVP) hydrogel (HG).

SMPs are polymeric smart materials that have the ability to return from a deformed state (temporary shape) to their original (permanent) shape induced by an external stimulus (trigger), such as temperature change. SMPs can retain two or more shapes, and the transition between those is induced by temperature. In addition to temperature change, the shape change of SMPs can also be triggered by an electric or magnetic field, light, or solvent plasticization. As well as polymers in general, SMPs also cover a wide property-range from stable to biodegradable, from soft to hard, and from elastic to rigid, depending on the structural units that constitute the SMP. SMPs include thermoplastic and thermoset (covalently cross-linked) polymeric materials.

Inclusion of a SMP in the complex is advantageous. A SMP including Hexamethylene diisocyanate (HDI), triethanolamine (TEA), and hydroxypropyl ethylenediamine (HPED) exhibited biocompatibility in a porcine side wall aneurysm, up to 100× volume expansion, is conformable to unique wound geometry, and has demonstrated occlusion in porcine hind limbs in less than 90 seconds. In an embodiment, when plasticized in 37° C. water, the glass transition temperature ($T_g$) is depressed to ~12° C. This allows for actuation when exposed to fluids at body temperature. In an embodiment the SMP foam was cleaned to remove unreacted reagents and reticulated to make an open pore structure. Pore sizes are tunable to between 200-1500 μm. In an embodiment the SMP foam is hydrophilic. Various embodiments have tuned hydrophilicity for the SMP so the devices actuate at different rates.

An HG is a network of polymer chains that are hydrophilic, sometimes found as a colloidal gel in which water is the dispersion medium. HGs are highly absorbent (they can contain over 90% water) natural or synthetic polymeric networks. HGs also possess a degree of flexibility very similar to natural tissue, due to their significant water content.

Inclusion of a PEG-DA-NVP HG in the complex is advantageous. Such an HG swells 20-100× its original mass in water, will complex with elemental iodine to form povidone-iodine ($PVP-I_2$) (Betadine) to provide antibacterial properties, and can be formulated to be biodegradable and biocompatible. Embodiments use various molecular weights of PEG, some with a high ratio of polyvinylpyrrolidone (PVP), which are thermally cured with excess hydrogel removed and then dried.

In an embodiment hydrophilic polyurethane SMP foams were cut into cylinders 8 mm in diameter and 20 mm in length. Then a PEG-DA hydrogel solution was complexed with iodine and cast into a PTFE mold containing the foam cylinders to create the SMP foam-HG composite. "Complexed" in this instance means the HG solution is mixed with iodine, and due to charges on some of the molecules in the HG, the iodine molecules are attracted by the HG branches essentially bonding the iodine to the PVP in the hydrogel. While the bond may not amount to a true covalent bond, there is a strong attraction between the two compounds that allows for a controlled release of iodine from the composite.

An embodiment of the complex of SMP and HG still retains the SM characteristics of the SMP alone (where Shape Recovery=(H"/H)(100) and H" is length after expansion and H is length before crimping). For example, a control SMP foam had a Pre Crimp Diameter (mm)=5.57, Crimped Diameter (mm)=0.74, Diameter after 15 min in 37° C. $H_2O$=5.39, and % Shape Recovery=96.8%. Similarly, a composite/complex of SMP foam and HG in an embodiment has Pre Crimp Diameter (mm)=5.89, Crimped Diameter (mm)=1.33, Diameter after 15 min in 37° C. $H_2O$=5.16, and % Shape Recovery=87.6%.

Also, an embodiment of the complex of SMP and HG has a strong ability to conform to and fill a wound area (where Expansion Ratio=(H"/H') and H" is length after expansion and H' is length after crimping). A control SM foam has an expansion ratio of 7.2 while a composite/complex of SMP foam and HG in an embodiment has an expansion ratio of 4.2.

Also, an embodiment of the complex of SMP and HG has strong swellability (where Q=(mass of saturated device)/(mass of dry device)), as evidenced by the following: SMP foam Q=1.1, SMP Foam-HG composite Q=23.6, and HG=29.1. Thus, in an embodiment addition of an HG to the SMP foam results in a 20× increase in fluid uptake in regards to a SMP foam alone.

Further, an embodiment of the SMP foam/HG complex provides adequate force applied to the wound boundary during expansion (see FIG. 1). As a result, the increase in constrained recovery force reduces the likelihood of device dislocation with a force that is not so excessive as to cause tissue damage. Dynamic Mechanical Analysis (DMA) was used for data collection for FIG. 1, which shows an increase in recovery force for embodiments including iodine and without iodine as compared to a control SMP foam.

Figure 2A:
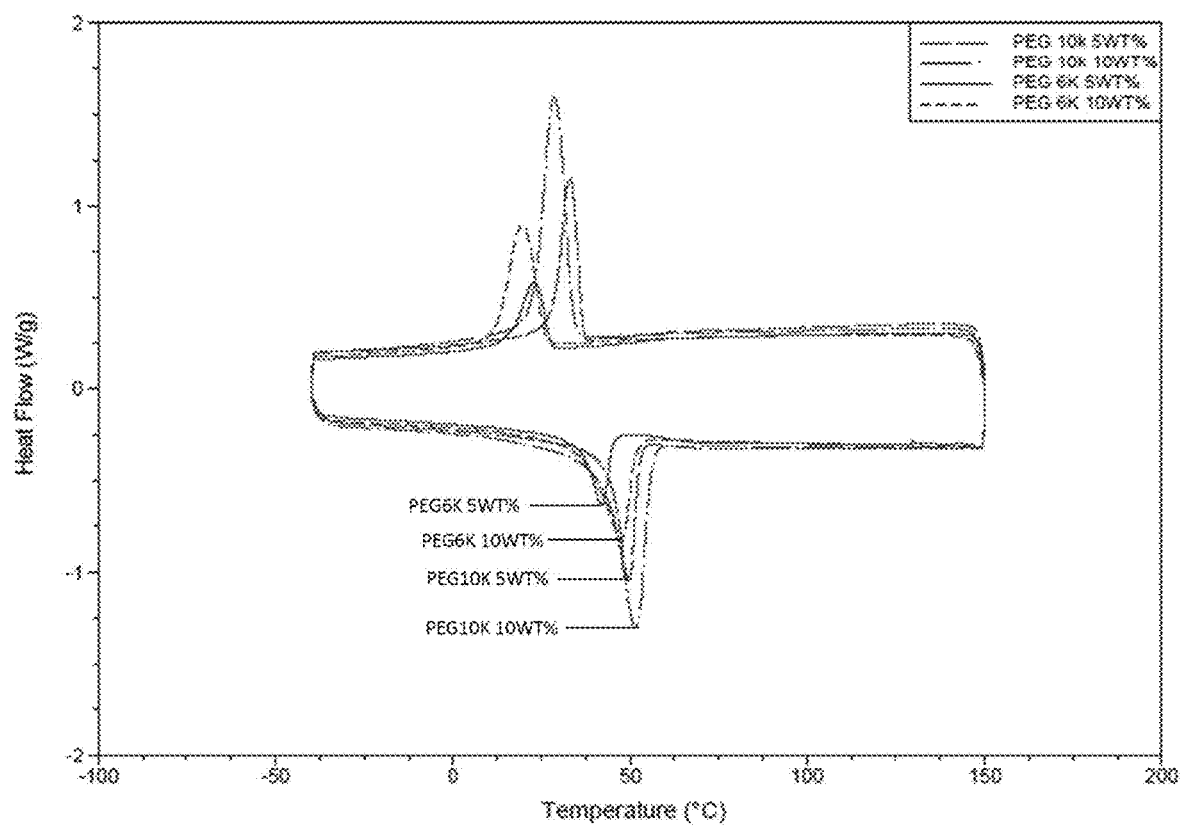

FIGS. 2(a) and 2(b) depict tunability of embodiments of the invention based on hydrogel composition, where thermograms are dominated by HG properties and Tg of SMP foams is ~67° C. when dry. These figures demonstrate the actuation temperature and Tg of the composite can be tuned via altering the molecular weight and concentration of the PEG in the HG. These figures show the thermomechanical properties of the HG remain intact after complexing with iodine and being incorporated into the composite.

Figure 3:
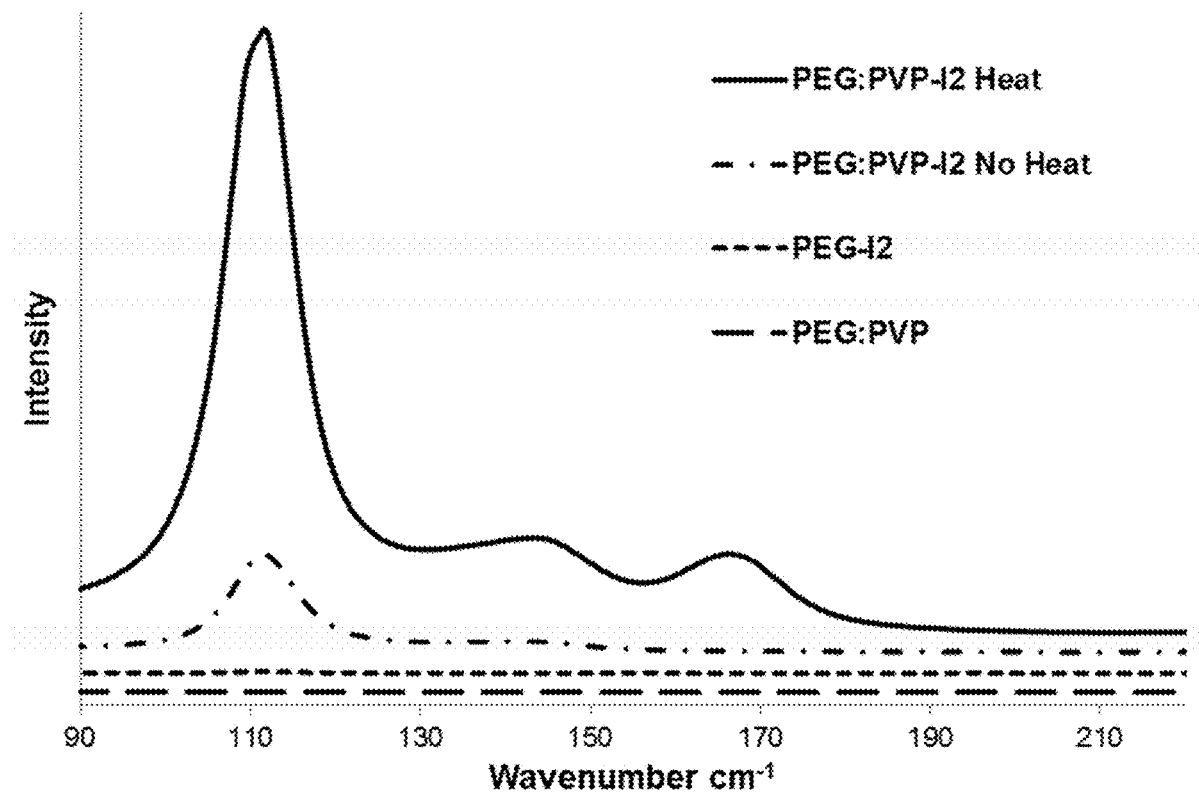
FIG. 3 depicting Raman spectroscopy results indicating that the SMP foam/HG complex shows spectral changes correlating to successful doping.
Figures 4A, 4B:
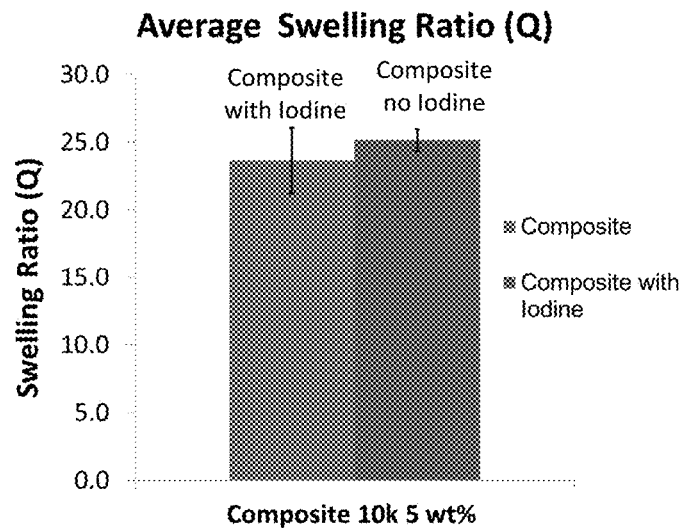
FIGS. 4(a) and 4(b) illustrate overall the iodine doped composites have a minimal effect on the physical properties of embodiments.

Further, in a bacterial adhesion study *Staphylococcus aureus* bacteria were incubated with HGs using a Cell Titer96® assay to quantify adherent bacteria. Iodine-doped HGs demonstrate antibacterial properties as opposed to HGs not including iodine. In an embodiment, iodine doping of the HG may be performed using heat and aqueous mixing of the HG materials with a subsequent brown coloration of the device. Using Raman spectroscopy a quantifiable method correlated with the presence of an Iodine complex wherein $I_3$ forms when bound to PVP (see FIG. 3) such that the SMP foam/HG complex shows spectral changes correlating to successful doping. In an embodiment the addition of iodine was shown to have no adverse effect on the physical properties of doped composites, wherein no substantive change was observed with respect to swelling ratio (where doped and undoped composites both exhibited about a 20× swelling increase over control SMP foam), percent recovery (where doped and undoped composites both exhibited a recovery of about 93%), and expansion rate (where doped and undoped composites both exhibited complete expansion within 2 minutes) (see also FIGS. 4(a) and (b)). Embodiments with Iodine provide self-sterilizing devices without changes in composite properties.

Thus, various embodiments provide a hemostatic wound dressing which: (a) retains its shape memory characteristics even after the introduction of hydrogel and iodine, (b) is inherently antibacterial to prevent infection if used in the field, (c) shows more than 20× increase in fluid uptake to absorb wound exudate and swells to 23× the original mass to allow exudate absorption and minimize potential bacteria colonization, (d) demonstrates more than 10× increase in recovery strength to prevent device dislocation, (e) easily deforms/conforms to fill complex wound geometry, (f) experiences more than 400% plastic strain recovery upon contact with blood to provide optimal volume filling, (g) is biocompatible.

An embodiment includes a kit having multiple SMP foam/HG composite devices such that more than one device may be employed to substantially fill a large wound or void or void having a particularly irregular shape. The kit may include gauze, wraps, and/or bandages to provide supplemental help in holding SMP foam/HG composite devices in place.

An embodiment employs the SMP foam/HG composite as a wound dressing. The device rapidly stops excessive internal and external bleeding, while also preventing bacterial infection by means of an antibacterial HG coating. The HG coating also enhances the SMP foam's ability to absorb fluid to aid in the wound healing process. The mechanical and thermal properties of the foam are tailored to meet the specific needs of specific wound geometries and locations (e.g., increased recovery force is required for higher flow, arterial bleeding conditions), and various antibacterial and thrombogenic compounds (e.g., kaolin, chitosan, silicate nanoparticles, bioactive glass particles, diatomaceous earth, and hydrogen peroxide) are easily combined with the HG coating to optimize the wound healing properties of the hemostatic foam device. The foams are heated above their $T_g$, held in the desired geometry for packaging, and cooled below their $T_g$ to retain their programmed shape until plasticized. The foams are either injected into or placed over the wound area, plasticized, and use their SM behavior to fill the entire, unique geometry of the wound. In an embodiment, the device applicator consists of a waterproof, sealed syringe that allows the devices to be injected directly into the wound volume. After placement, hemostasis occurs in less than five minutes in some embodiments, while the antibacterial properties of the foam act immediately upon contact with the wound surface.

In an embodiment the syringe or applicator is sealed to prevent any premature device actuation. The applicator may include numerous composite devices (e.g., SMP foam/HG beads). In embodiment the applicator also deposits an additional antibacterial agent (e.g., hydrogen peroxide) when the device(s) are released into the wound. This applicator may include a double barrel syringe where the composite devices do not mix with the additional antibacterial agent until both the composite devices and the additional antibacterial agent have exited the applicator.

Embodiments can be used to replace or augment conventional gauze to treat hemorrhage and absorb fluid in surgical applications, as well as an alternative to current hemostatic sponge products used throughout the military and civilian emergency response units to treat traumatic injuries and control extreme hemorrhage. Aside from military and first-responder use, these SMP foam/HG composites may be used to help treat diabetic ulcers and encourage reendothelialization and proper healing of open sores. The SMP foam may act as a tissue scaffold and encourage connective tissue infiltration and subsequent endothelial cell growth and proliferation within the sore.

A significant aspect of various embodiments is their ability to be used in many traumatic injuries where hemorrhage is involved. Such embodiments are not limited by their ability to only prevent bleeding in certain applications or wound types. This results in a universal product to treat any form or most forms of uncontrolled bleeding. This allows first-responders to stabilize traumatic injury patients before arriving at the hospital, and provides an easy-to-use, effective means for soldiers to stop the excessive bleeding of a fellow soldier or themselves. With uncontrolled hemorrhage being the cause of more than 50% of deaths in the battlefield and civilian trauma centers, these SMP foam/HG devices will save lives of individuals who would otherwise die as a result of exsanguination.

This stands in contrast to current hemostatic sponges that are used for internal or external bleeding, often without any antimicrobial properties.

In contrast, conventional hemostatic sponge products used to control bleeding cannot be implanted. Such products have to be removed from the wound bed after a few hours. Alternatively, injectable foams (e.g., soap foam and the like) that are used to control internal bleeding during surgery are not used for exposed, external wounds because of the potential for bacterial infection and their limited mechanical integrity/properties. However, an embodiment of the SMP foam/HG composite has the mechanical strength (e.g., from the SMP foam and/or HG) and antibacterial properties (e.g., from iodine infused HG) to allow external use and internal use due to the biocompatibility of the SMP foam and HG and the antibacterial component of various embodiments.

Also, conventional hemostatic sponge products must be frequently changed as a result of potential bacterial and fungal infections. But SMP foam/HG embodiments described herein can also be used to control both internal and external bleeding. In addition, the ability to conform to any size and shape of a wound to provide complete coverage is unique to embodiments described herein. This provides more robust wound coverage that can withstand arterial blood flow pressures, allows one device to be used to treat a vast array of injury sites and size of wound, does not require device placement in a specific location inside the wound, and ensures that healthy tissue is isolated from damaged tissue.

In various embodiments the HG/SMP foam are combined in various ways. For example, in one embodiment they are combined simply by submerging the SMP foam into an HG solution, withdrawing the SMP foam from the solution, and then heating the SMP/HG combination to crosslink the hydrogel. In another embodiment, the SMP foam is placed in a mold (e.g., a hole drilled into a block of polymer with the same diameter as the foam). A HG solution is then poured into the mold. The combination is then heated to crosslink the hydrogel.

In an embodiment, the HG is found throughout the SMP foam or various portions of the SMP foam. The HG deposits in small portions on struts of the SMP foam and/or forms a thin membrane on the struts (see FIG. 6(b), wherein the scale in the background is in cm). The HG may also fill the entire volume (or almost the entire volume) of the foam (see FIG. 6(a), wherein the scale in the background is in cm). In an embodiment small pieces of SMP/HG complex (e.g., beads) are injected into a wound provided those pieces are large enough to avoid entering into and being communicated within a patient's vasculature. Such an embodiment may allow for a higher HG concentration to increase the moisture absorption capacity of the foam. In another embodiment, the SMP/HG combination device is attached to a bandage so the device is placed in the wound and then pressed against the wound based on the bandage pressing against the patient.

Figure 6A:
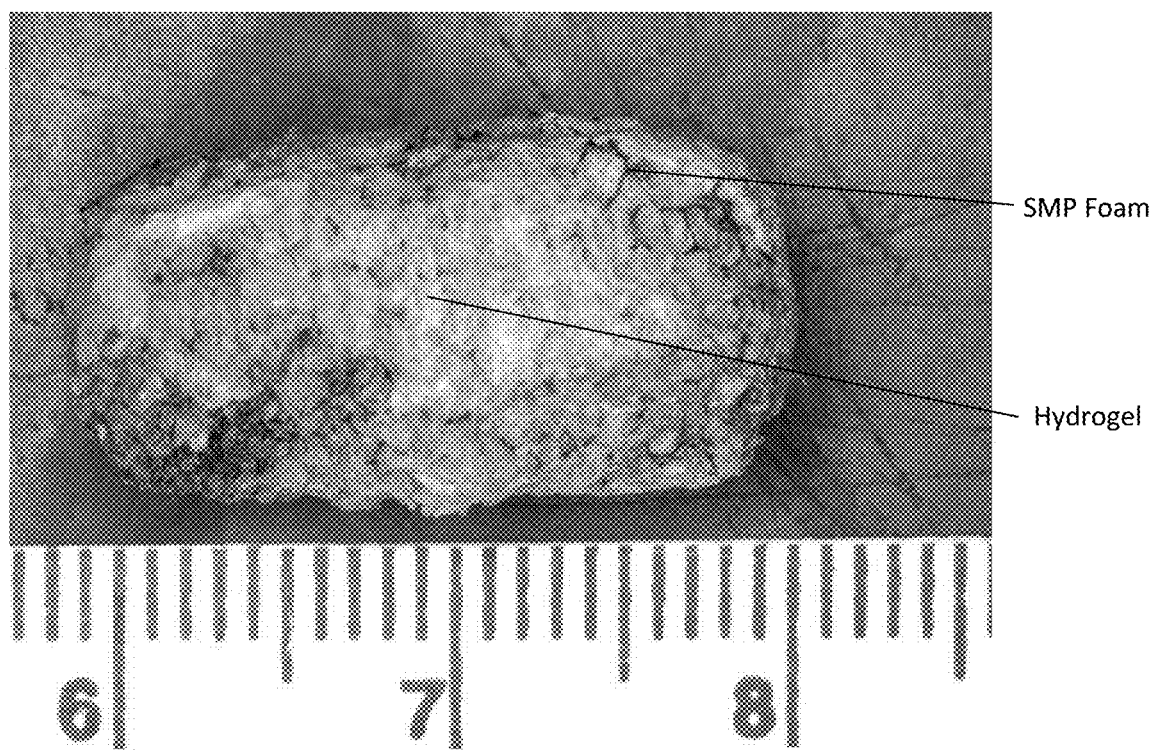
FIGS. 6(a) and (b) are images of embodiments of the invention.
Figure 6B:
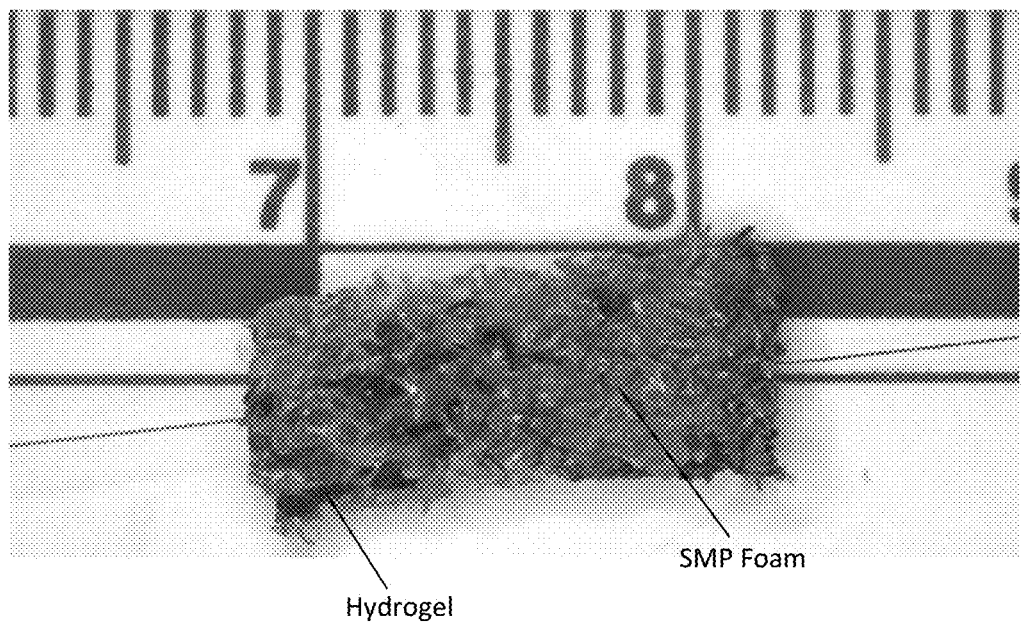

In an embodiment a kit may include embodiments such as those of FIGS. 6(a) and 6(b). In such a case the preferred embodiment between the embodiments of FIGS. 6(a) and 6(b) depends on the therapeutic goal. For example, the embodiment of FIG. 6(b) may expand more rapidly than that of FIG. 6(a) but the HG may more easily decouple from the foam. The HG of FIG. 6(a) may be more stable within the foam and be more resistant to decoupling from the foam than that of FIG. 6(b). A kit may provide instructions to a user to initially utilize the embodiment of FIG. 6(b) and then to follow such treatment by utilizing the embodiment of FIG. 6(a).

In an embodiment, the SMP foam is covered with iodine-doped HG solution and then heated to crosslink the HG about the SMP foam. Upon crosslinking, the HG adheres to the foam struts.

A method includes the following: (1) the SMP foam/HG device is heated above its $T_g$ and held in the desired geometry for packaging; (2) the device is cooled below its $T_g$ to program the packaged shape into the device; (3) the device is sterilized under EtO sterilization and packaged and stored at temperatures less than 30 degrees Celsius; (4) to apply the hemostatic sponge, it is removed from the package and inserted anywhere within the wound area; (5) the wound area is covered with a cloth, bandage, or hydrogel graft and the foam plasticizes at body temperature to expand and fill the entire geometry of the wound; and (6) pressure is applied until hemostasis is observed.

An embodiment includes a SMP foam/HG composite comprising isocyanate, hexamethylene diisocyanate (HDI), trimethyl hexamethylene diisocyanate (TMHDI), N,N,N',N'-tetrakis(hydroxypropyl)ethylenediamine (HPED), triethanolamine (TEA), isophorone diisocyanate (IPDI), polyethylene glycol (PEG) diacrylate (DA), polyethylene diacryamide, PEG diacrylamide-N-vinylpyrrolidone (NVP), hyaluronic acid, poly(2-hydroxyethyl methacrylate) (polyHEMA), polyvinyl alcohol (PVA), polyvinyl acetate (PVAc), iodine, deoionized water, 3-sulfopropyl acrylate potassium salt, 2-hydroxyethyl acrylate, polypropylene glycol diacrylate, ethylene glycol dimethacrylate, tetra(ethylene glycol) diacrylate, thrombin, azobisisobutyronitrile, benzoyl peroxide, 2,2-dimethoxy-2-phenylacetophenone, butanediol, propanediol, pentanediol, diethyleneglycol, dipropylene glycol, diethanolamine, dibutalene glycol, hexamethylenediamine, hydrogenated 4,4'-Methylenebis(cyclohexyl isocyanate), PEG diacrylamide—NVP and other compositions.

An embodiment includes a SMP foam/HG composite comprising HDI, HPED, TEA, PEG-DA, NVP, iodine, and deionized water.

An embodiment includes a SMP foam/HG composite comprising HDI, HPED, TEA, PEG-DA, NVP, hyaluronic acid, iodine, and deionized water.

An embodiment includes a SMP foam/HG composite comprising TMHDI, HPED, TEA, PEG-DA, NVP, hyaluronic acid, iodine, and deionized water.

An embodiment includes a SMP foam/HG composite comprising TMHDI, HPED, TEA, PEG-DA, NVP, iodine, and deionized water.

An embodiment includes a SMP foam/HG composite comprising IPDI, HPED, TEA, PEG-DA, NVP, hyaluronic acid, iodine, and deionized water.

An embodiment includes a SMP foam/HG composite comprising IPDI, HPED, TEA, PEG-DA, NVP, iodine, and deionized water.

An embodiment includes a SMP foam/HG composite comprising HDI, HPED, TEA, PEG-DA, polyHEMA, NVP, iodine, and deionized water.

An embodiment includes a SMP foam/HG composite comprising HDI, HPED, TEA, PEG-DA, NVP, thrombin, iodine, and deionized water.

An embodiment includes a SMP foam/HG composite comprising HDI, HPED, TEA, PEG-DA, NVP, thrombin, hyaluronic acid, iodine, and deionized water.

In an embodiment the SMP foam includes a crosslinked thermoset polyurethane polymer comprising a covalently bonded network structure and a reaction product of an aliphatic diisocyanate monomer reacted with at least one symmetric hydroxyl containing monomer; wherein said polymer has shape memory behavior and is formed into a permanent primary shape, re-formed into a stable secondary shape, and is configured to be controllably actuated to recover said permanent primary shape; wherein the diisocyanate monomer and the at least one symmetric hydroxyl containing monomer are formulated to a 1:1 ratio of isocyanate to hydroxyl functional groups; wherein the at least one symmetric hydroxyl containing monomer includes at least one of N,N,N',N'-tetrakis (2-hydroxypropyl) ethylenediamine (HPED) and triethanol amine (TEA); wherein the polymer has a Young's modulus in a range of 1 to 100 MPa at a temperature above a glass transition temperature of the polymer.

In an embodiment an HG is grafted to a SMP foam surface as well.

In an embodiment wherein the diisocyanate monomer includes HDI, and the at least one symmetric hydroxyl containing monomer includes HPED and TEA. In an embodiment the diisocyanate monomer is symmetric in structure. In an embodiment the HDI composes between 53-61 weight % of the polymer, the HPED composes between 10-47 weight % of the polymer, and the TEA composes less than 29 weight % of the polymer.

Figure 5A:
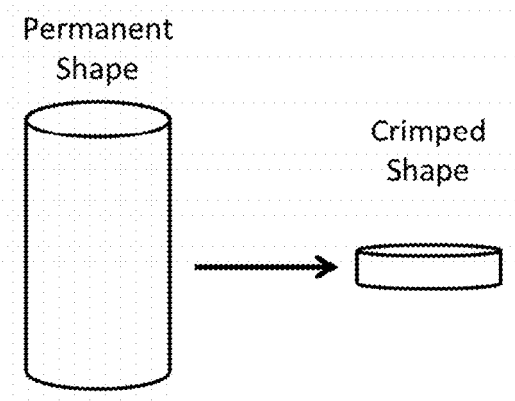
FIGS. 5(a), (b), and (c) illustrate pre-crimp (permanent shape) and post-crimp (secondary shape) embodiments of the invention.
Figure 5B:
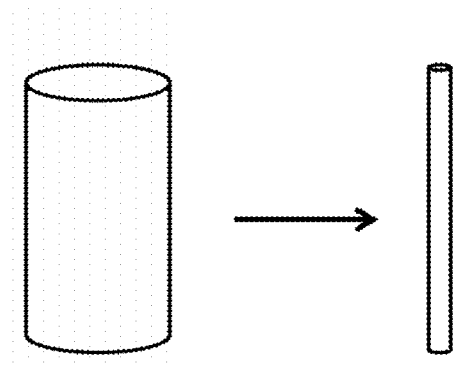
Figure 5C:
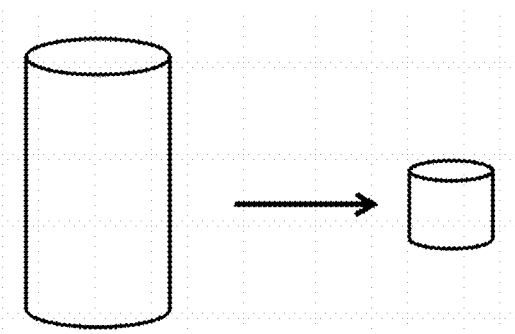

FIGS. 5(a), (b), and (c) illustrate pre-crimp (permanent shape) and post-crimp embodiments of the invention. As shown therein, in FIG. 5a the post-crimp image is generally planar whereas FIGS. 5(b) and (c) show post-crimp images that are cylindrical with FIG. 5(b) being straw-like and FIG. 5(c) being pellet-like. All three post-crimp forms result in the same permanent cylindrical shape. However in other embodiments a permanent and/or post-crimp shape may be rectangular, ovular, spherical, and the like.

The following examples pertain to further embodiments. Example 1 includes a wound dressing comprising: a shape memory polymer (SMP) foam, including open cells, having first and second states; and a hydrogel (HG) included within the cells; wherein (a) in a first position a composite, including the SMP foam and the HG, is configured to be located proximate a wound with the SMP foam in the first state; (b) in a second position the composite is configured to expand to the second state within the wound when the SMP foam is plasticized at 37° C. depressing a glass transition temperature ($T_g$) of the SMP foam to below 25° C.

For example, "when the SMP foam is plasticized at 37° C." includes plasticization across a spectrum of temperatures. For example, plasticization may occur over a range of temperatures such as, for example, from 33° C. to 40° C. wherein 37° C. is included therein but where plasticization also occurs at 35° C. and 39° C. Further, "depressing a glass transition temperature ($T_g$) of the SMP foam to below 25° C." includes depressing the $T_g$ to, for example, 24, 23, 22, 21, 20, 19, 18, 17, 16, 15, 14, 13, 12, 11, 10, 9, 8, 7, 6, 5, 4, 3, 2, 1, 0° C. and the like. A HG "included within the cells" includes, for example, HG completely filling a cell, partially filling a cell, or coating a strut of a cell. Further, "proximate a wound" includes external and internal applications applying to, for example, lacerations of the skin as well as lacerations that are internal to a patient (e.g., a wound in the liver intentionally caused by a surgeon's scalpel) and caused by surgery and/or trauma.

In example 2 the subject matter of the Example 1 can optionally include wherein the SMP foam includes polyurethane and the HG includes Poly(ethylene gylcol) Diacrylate (PEG-DA) N-vinylpyrrolidone (NVP) (PEG-DA-NVP HG).

In example 3 the subject matter of the Examples 1-2 can optionally include wherein the SMP foam includes two or more members selected from the group comprising Hexamethylene diisocyanate (HDI), triethanolamine (TEA), and hydroxypropyl ethylenediamine (HPED).

For example, an embodiment includes TEA and HDI but no HPED. Another embodiment may include HPED and HDI but not TEA. Of course other embodiments are not so constrained and may include all three of HPED, HDI, and TEA, only one of those, or none of those.

In example 4 the subject matter of the Examples 1-3 can optionally include wherein the SMP foam actuates at body temperature.

As used herein, "body temperature" is meant to convey a normal body temperature range. Normal body temperature varies by person, age, activity, and time of day. The average normal body temperature is generally accepted as 98.6° F. (37° C.) however the "normal" body temperature can have a wide range, from 97° F. (36.1° C.) to 99° F. (37.2° C.). A temperature over 100.4° F. (38° C.) may indicate a fever but would still be a condition within the range of example 4.

In example 5 the subject matter of the Examples 1-4 can optionally include wherein the HG is doped with an antimicrobial agent.

Doping in this context conveys the agent is added to the HG with no specific chemical bond necessarily implied.

In example 6 the subject matter of the Examples 1-5 can optionally include wherein the antimicrobial agent includes iodine.

As used in this context "iodine" includes derivatives therefrom.

In example 7 the subject matter of the Examples 1-6 can optionally include wherein the iodine is bound to polyvinylpyrrolidone (PVP) included in the HG.

In example 8 the subject matter of the Examples 1-7 can optionally include a member selected from the group comprising: kaolin, chitosan, silicate nanoparticles, bioactive glass particles, diatomaceous earth, and hydrogen peroxide.

In example 9 the subject matter of the Examples 1-8 can optionally include a syringe that includes the composite and a plurality of additional composites, each of the additional composites including an additional SMP foam with additional cells that include additional HGs.

For example, an embodiment may include SMP foam/HG beads to be deployed from a syringe.

In example 10 the subject matter of the Examples 1-9 can optionally include wherein the SMP foam is configured to conform to contours of the wound, when in the second position and the second state, based on the SMP foam having % Shape Recovery greater than 100, expansion ratio greater than 4, and swellability (Q) greater than 20 where Q=(mass of saturated device)/(mass of dry device).

Embodiments cover a variety of scenarios including, for example, % Shape Recovery=80, 85, 90, 95, 100, 105, 110, 115, 120, 125 and the like, Expansion Ratio=1.00, 2.00, 3.00, 4.00, 5.00, 6.00, 7.00, 8.00, 9.00, 10.00 and the like, and Q=18, 19, 20, 21, 22, 23, 24, 25, 26, 27, 28, 29, 30, 31, 32 and the like.

In example 11 the subject matter of the Examples 1-10 can optionally include wherein the cells are reticulated.

For example, the reticulation may be partial or full.

In example 12 the subject matter of the Examples 1-11 can optionally include wherein (a) the SMP foam and HG are both biodegradable, and (b) the composite is a medical implant configured for permanent implantation within a patient until the composite biodegrades within the patient.

In another version of example 12 the subject matter of the Examples 1-11 can optionally include wherein the SMP foam and HG are both biostable, and the composite is a medical implant configured for permanent implantation within a patient.

As used herein, "biostable" means the biostable element does not degrade within the body.

In example 13 the subject matter of the Examples 1-12 can optionally include wherein the SMP foam is crosslinked and includes struts, which form the cells, and the HG is crosslinked around struts.

For example, in an embodiment the HG is not crosslinked until it is already impregnated within the foam. In the same embodiment the foam is crosslinked before the HG is impregnated within the foam. As a result, "HG is crosslinked around struts" provides for mechanical stability considering the HG is actually formed around the struts and then crosslinked in that same position. In such an embodiment, a completely polymerized, reticulated, cleaned, and dried foam is provided and then exposed to a HG solution. The foam/HG solution is then heated to completely crosslink the HG while the HG is on the foam.

In example 14 the subject matter of the Examples 1-13 can optionally include wherein the SMP foam is a thermoset polymer that includes polyurethane.

In example 15 the subject matter of the Examples 1-14 can optionally include wherein in the first state the composite is generally cylindrical.

In example 16 the subject matter of the Examples 1-15 can optionally include wherein in the first state the composite is generally spherical.

In example 17 the subject matter of the Examples 1-16 can optionally include wherein in the first state the composite is generally planar.

An embodiment is represented in FIG. 5(a), which actuates more quickly than other configurations. Some of the shapes are easier to crimp or form the "first state" of example 1 than others while still others may actuate to the "second state" more readily than others.

Example 18 includes a hemorrhage management system comprising: a shape memory polymer (SMP) foam, including open cells, having first and second states; and a hydrogel (HG) included within the cells; wherein (a) in a first position a composite, including the SMP foam and the HG, is configured to be located proximate a hemorrhagic tissue with the SMP foam in the first state; (b) in a second position the composite is configured to be expanded to the second state against the hemorrhagic tissue when the SMP foam is plasticized at 37° C. depressing a glass transition temperature ($T_g$) of the SMP foam to below 25° C.

As used herein, a "hemorrhagic tissue" includes tissues that bleed slightly, profusely, and all points in between.

In example 19 the subject matter of Example 18 can optionally include a substrate coupled to the composite, wherein the substrate includes a member selected from the group comprising gauze, bandage, and a tourniquet.

For example, the coupling may be fixed (which can be "undone" without using destructive force) or permanent (which cannot be "undone" without using destructive force). The composite may extend in a rectangular "first state" along the underside of a gauze or adhesive bandage such that a user simply applies the bandage over a wound as one would do in a conventional manner and then allow the composite to actuate to the second state where the SMP foam expands and the HG swells.

In another version of example 19 the subject matter of Example 18 can optionally include a substrate coupled to the composite, wherein the substrate includes a member selected from the group comprising gauze, bandage, hydrogel, skin substitute, and a tourniquet.

In example 20 the subject matter of the Examples 18-19 can optionally include wherein (a) the SMP foam is cross-linked and includes struts, which form the cells, and the HG is crosslinked around struts; and (b) the SMP foam is a thermoset polymer that includes polyurethane.

The foregoing description of the embodiments of the invention has been presented for the purposes of illustration and description. It is not intended to be exhaustive or to limit the invention to the precise forms disclosed. Persons skilled in the relevant art can appreciate that many modifications and variations are possible in light of the above teaching. Persons skilled in the art will recognize various equivalent combinations and substitutions for various components shown in the Figures. It is therefore intended that the scope of the invention be limited not by this detailed description, but rather by the claims appended hereto.

Although the description above contains many details and specifics, these should not be construed as limiting the scope of the application but as merely providing illustrations of some of the presently preferred embodiments of the apparatus, systems, and methods. Other implementations, enhancements and variations can be made based on what is described and illustrated in this patent document. The features of the embodiments described herein may be combined in all possible combinations of methods, apparatus, modules, systems, and computer program products. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments.

Therefore, it will be appreciated that the scope of the present application fully encompasses other embodiments which may become obvious to those skilled in the art. In the claims, reference to an element in the singular is not intended to mean "one and only one" unless explicitly so stated, but rather "one or more." All structural and functional equivalents to the elements of the above-described preferred embodiment that are known to those of ordinary skill in the art are expressly incorporated herein by reference and are intended to be encompassed by the present claims. Moreover, it is not necessary for a device to address each and every problem sought to be solved by the present apparatus, systems, and methods, for it to be encompassed by the present claims. Furthermore, no element or component in the present disclosure is intended to be dedicated to the public regardless of whether the element or component is explicitly recited in the claims. No claim element herein is to be construed under the provisions of 35 U.S.C. 112, sixth paragraph, unless the element is expressly recited using the phrase "means for."

While the apparatus, systems, and methods may be susceptible to various modifications and alternative forms, specific embodiments have been shown by way of example in the drawings and have been described in detail herein. However, it should be understood that the application is not intended to be limited to the particular forms disclosed. Rather, the application is to cover all modifications, equivalents, and alternatives falling within the spirit and scope of the application as defined by the following appended claims.

The invention claimed is:

1. A system comprising:
    a shape memory polymer (SMP) foam, including open cells, having first and second states; and
    a hydrogel (HG) included within the cells;
    wherein (a) in a first position a composite, including the SMP foam and the HG, is configured to be located in a wound with the SMP foam in the first state; (b) in a second position the composite is configured to expand to the second state in the wound when the SMP foam is plasticized at 37° C. depressing a glass transition temperature (Tg) of the SMP foam to below 25° C.

2. The system of claim 1, wherein the SMP foam includes polyurethane and the HG includes Poly(ethylene glycol) Diacrylate (PEG-DA) N-vinylpyrrolidone (NVP) (PEG-DANVPHG).

3. The system of claim 2, wherein the SMP foam includes at least two of Hexamethylene diisocyanate (HDI), triethanolamine (TEA), hydroxypropyl ethylenediamine (HPED), or combinations thereof.

4. The system of claim 1, wherein the SMP foam actuates at body temperature.

5. The system of claim 3, wherein the HG includes an antimicrobial agent.

6. The system of claim 5, wherein the antimicrobial agent includes iodine.

7. The system of claim 1, wherein:
the HG includes iodine and polyvinylpyrrolidone (PVP); and
the iodine is bound to the PVP.

8. The system of claim 1 comprising an applicator that includes the composite and a plurality of additional composites, each of the additional composites including an additional SMP foam with additional cells that include additional HGs.

9. The system of claim 1, wherein the SMP foam is configured to conform to contours of the wound, when in the second position and the second state, based on the SMP foam having a % Shape Recovery greater than 85, an expansion ratio greater than 4.00, and a swellability (Q) greater than 20 where Q=(mass of saturated device)/(mass of dry device).

10. The system of claim 1, wherein:
the SMP foam is crosslinked;
the SMP foam includes struts;
the struts form the cells, and
the HG is crosslinked around the struts.

11. The system of claim 1, wherein the SMP foam is a thermoset polymer that includes polyurethane.

12. A medical implant system comprising:
a shape memory polymer (SMP) foam having open cells; and
a hydrogel (HG) included within the cells;
wherein the SMP foam plasticizes at 37° C. to depress a glass transition temperature (Tg) of the SMP foam to below 25° C.;
wherein the SMP foam is crosslinked and includes struts;
wherein the struts form the open cells;
wherein the HG is crosslinked around the struts.

13. The medical implant system of claim 12, wherein the SMP foam is a thermoset polymer that includes polyurethane.

14. The medical implant system of claim 13, wherein the SMP foam includes at least two of Hexamethylene diisocyanate (HDI), triethanolamine (TEA), hydroxypropyl ethylenediamine (HPED), or combinations thereof.

15. The medical implant system of claim 14, wherein the HG includes Poly(ethylene glycol) Diacrylate (PEG-DA) N-vinylpyrrolidone (NVP) (PEG-DANVPHG).

16. The medical implant system of claim 12, wherein:
the SMP foam includes polyurethane;
the HG includes iodine and polyvinylpyrrolidone (PVP); and
the iodine is bound to the PVP.

17. A method comprising:
providing a shape memory polymer (SMP) foam having open cells, wherein (a) the SMP foam is crosslinked and includes struts, and (b) the struts form portions of the open cells;
inserting a hydrogel (HG) into the open cells; and
heating the SMP foam and the HG to crosslink the HG around the struts;
wherein the SMP foam plasticizes at 37° C. to depress a glass transition temperature (Tg) of the SMP foam to below 25° C.

18. The method of claim 17, wherein the SMP foam is a thermoset polymer that includes polyurethane.

19. The method of claim 18, wherein the HG includes Poly(ethylene glycol) Diacrylate (PEG-DA) N-vinylpyrrolidone (NVP) (PEG-DANVPHG).

20. The method of claim 19, wherein the SMP foam includes at least two of Hexamethylene diisocyanate (HDI), triethanolamine (TEA), hydroxypropyl ethylenediamine (HPED), or combinations thereof.

* * * * *